US009395322B2

(12) United States Patent
Buck, Jr. et al.

(10) Patent No.: US 9,395,322 B2
(45) Date of Patent: Jul. 19, 2016

(54) METHODS OF SCALING DATA USED TO CONSTRUCT BIOSENSOR ALGORITHMS AS WELL AS DEVICES, APPARATUSES AND SYSTEMS INCORPORATING THE SAME

(71) Applicant: Roche Diabetes Care, Inc., Indianapolis, IN (US)

(72) Inventors: Harvey B. Buck, Jr., Indianapolis, IN (US); Scott E. Carpenter, Pendleton, IN (US); Zheng Zheng Pan, Plano, TX (US); Rene Valverde-Ventura, Carmel, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/851,444

(22) Filed: Sep. 11, 2015

(65) Prior Publication Data
US 2016/0041117 A1    Feb. 11, 2016

Related U.S. Application Data

(63) Continuation of application No. PCT/EP2014/054952, filed on Mar. 13, 2014.

(60) Provisional application No. 61/794,280, filed on Mar. 15, 2013.

(51) Int. Cl.
*G01N 27/327* (2006.01)
*G01N 27/10* (2006.01)

(52) U.S. Cl.
CPC ............ *G01N 27/3274* (2013.01); *G01N 27/10* (2013.01)

(58) Field of Classification Search
CPC ... G01N 27/327; G01N 27/10; G01N 33/487; A61B 5/05
See application file for complete search history.

(56) References Cited

U.S. PATENT DOCUMENTS

| | | | |
|---|---|---|---|
| 2003/0060692 A1 | 3/2003 | Ruchti et al. | |
| 2004/0157339 A1* | 8/2004 | Burke | G01N 27/3274 436/149 |
| 2005/0279631 A1 | 12/2005 | Celentano | |
| 2007/0102292 A1 | 5/2007 | Dreibholz et al. | |
| 2009/0030641 A1 | 1/2009 | Fjield et al. | |
| 2010/0170807 A1* | 7/2010 | Diebold | G01N 27/3274 205/792 |

FOREIGN PATENT DOCUMENTS

| | | |
|---|---|---|
| EP | 1156324 A1 | 11/2001 |
| EP | 2042865 A2 | 4/2009 |

(Continued)

OTHER PUBLICATIONS

Gunasingham; et al., "Pulsed amperometric detection of glucose using a mediated enzyme electrode", Journal of Electroanalytical Chemistry and Interfacial Electrochemistry, Jul. 25, 1990, vol. 287, No. 2, pp. 349-362.

*Primary Examiner* — Jennifer Dieterle

(57) ABSTRACT

Methods are disclosed for scaling body fluid analysis data to correct and/or compensate for confounding variables such as hematocrit (Hct), temperature, variations in electrode conductivity or combinations thereof before providing an analyte concentration. The scaling methods utilize current response data obtained from an AC block applied prior to a DC block to minimize the impact of such confounding variables upon the observed DC current response before creating descriptors or algorithms. The scaling methods therefore compensate the measured DC current by using data from the AC block made on the same sample. Also disclosed are devices, apparatuses and systems incorporating the various scaling methods.

10 Claims, 20 Drawing Sheets

(56) References Cited

FOREIGN PATENT DOCUMENTS

| EP | 2138841 A2 | 12/2009 |
| EP | 2261646 B1 | 7/2015 |
| WO | 9932881 A1 | 7/1999 |
| WO | 0121827 A1 | 3/2001 |
| WO | 03060154 A2 | 7/2003 |
| WO | 2006109279 A2 | 10/2006 |
| WO | 2007100651 A1 | 9/2007 |
| WO | 2008036516 A1 | 3/2008 |
| WO | 2009075951 A1 | 6/2009 |
| WO | 2012134890 A1 | 10/2012 |

* cited by examiner

METHODS OF SCALING DATA USED TO CONSTRUCT BIOSENSOR ALGORITHMS AS WELL AS DEVICES, APPARATUSES AND SYSTEMS INCORPORATING THE SAME

CROSS-REFERENCE TO RELATED APPLICATIONS

This patent application is a continuation of Int'l Patent Application No. PCT/EP2014/054952 (filed 13 Mar. 2014), which claims priority to and the benefit of U.S. Provisional Patent Application No. 61/794,280 (filed 15 Mar. 2013). Each patent application is incorporated herein by reference as if set forth in its entirety.

TECHNICAL FIELD

The disclosure relates generally to mathematics and medicine, and more particularly, it relates to methods of scaling body fluid analysis measurement data to correct and/or compensate for confounding variables such as hematocrit (Hct), temperature, raw material variations such as electrode conductivities or a combination thereof before providing an analyte concentration.

BACKGROUND

Many analyte measurement systems, such as self-monitoring blood glucose (SMBG) systems, clinical blood glucose monitoring systems and laboratory blood glucose monitoring systems, are based upon an amperometric, coulometric, potentiometric, voltammetric, or other electrical measurement of an electro-active species produced by a reaction with an analyte such as glucose or the measurement of a direct property of the analyte matrix. A combination of these methods also can be employed for calculating an analyte concentration.

In SMBG systems, an electrochemical measurement typically is performed by inserting a biosensor into a handheld meter and introducing a drop of a fluidic sample such as blood onto the biosensor having a defined sample space, a dried chemical reagent and a system of electrodes. Upon detecting the sample, the meter then performs the electrochemical measurement, and mathematical algorithms convert the response data into a reliable glucose concentration.

For example, in a single-potential, DC-based amperometric measurement, a potential is applied to a fluidic sample containing an electro-active analyte, and current is monitored as the analyte is reduced or oxidized. The resulting DC current exhibits a time decay, as described by the Cottrell equation. As the slope of the decay decreases and approaches a constant rate of change with respect to time, the magnitude of the current can be used to quantify the analyte.

The magnitude, rate and shape of the current decay, however, can be influenced by many variables including, but not limited to, reagent thickness, wetting of the reagent, rate of sample diffusion, Hct and temperature as well as presence of certain interferents. These interferents, or confounding variables, can cause an increase or decrease in the observed magnitude of the DC current that is proportional to an analyte such as glucose, thereby causing a deviation from the "true" glucose concentration.

Current methods and systems provide some advantages with respect to convenience; however, there remains a need for measurement methods that can correct or otherwise compensate for confounding variables.

BRIEF SUMMARY

In view of the disadvantages noted above, the disclosure describes methods of compensating or correcting for an effect that certain confounding variables may have in measuring an analyte concentration in a fluidic sample, thereby providing a "true" analyte concentration. The methods are based upon an inventive concept that includes using information derived from alternating current (AC) responses to scale data from higher amplitude responses (such as DC measurements) in a manner that reduces the impact of confounding variables before using algorithms that provide an analyte concentration. The inventive concept therefore provides certain advantages, effects, features and objects when compared to known methods of measuring an analyte concentration in a fluidic sample.

In one aspect, a scaling method is provided to compensate or correct for variations in electrode conductivity. The method includes a step of measuring at least two loop resistances of an electrode system on a biosensor, normalizing each of the at least two loop resistances by dividing each by a separate constant, and scaling the current responses by incorporating a lower (i.e., smallest) of the normalized loop resistances into an algorithm for determining an analyte concentration or into a failsafe. The method also includes steps of applying to a body fluid sample a test sequence having an AC block and at least one DC block and measuring AC and DC current responses.

One of the at least two loop resistances can be measured from contact pads associated with a conductive trace of a working electrode. Another of the at least two loop resistances can be measured from contact pads associated with a conductive trace of a counter electrode.

Each constant that is used to normalize the loop resistances can be a pre-determined median resistance value that was obtained by measuring respective loop resistances in one or more batches/lots of biosensors.

With respect to the AC block, it can be a block of low-amplitude signals applied sequentially or simultaneously in parallel. In some instances, the AC block includes at least two different low-amplitude signals. For example, the AC block can include two (2) segments at two (2) frequencies such as, for example, about 10 kHz or about 20 kHz followed by about 1 kHz or about 2 kHz. In other instances, the AC block includes a plurality of low-amplitude signals. For example, the AC block can have five (5) segments at four (4) frequencies such as, for example, about 10 kHz, about 20 kHz, about 10 kHz, about 2 kHz and about 1 kHz. Alternatively, the AC block can have four (4) segments at four (4) frequencies such as, for example, about 20 kHz, about 10 kHz, about 2 kHz and about 1 kHz. Alternatively, the AC block can have four (4) frequencies applied simultaneously at about 10 kHz, about 20 kHz, about 10 kHz, about 2 kHz and about 1 kHz. Alternately still, the AC block can have a multi-frequency excitation waveform that simultaneously applies desired low-amplitude AC signals.

In some instances, the AC block is applied for about 500 msec to about 1.5 sec. In other instances, the AC block is applied for about 100 msec to about 300 msec.

With respect to the DC block, it can include at least one (1) pulse to about ten (10) pulses at a potential that alternates between about 0 mV to about +450 mV. In some instances, the DC block can be a single potential step from about 0 mV to about +450 mV, where the potential is maintained so that a decaying current response may be detected. That is, the DC block includes at least one excitation pulse and at least one recovery pulse, where the pulses alternate between about 0 mV to about +450 mV.

Regardless of the number of pulses, each DC pulse can be applied for about 50 msec to about 500 msec. For example, each DC pulse at +450 mV can be applied for about 250 msec, and each DC pulse at 0 mV can be applied for about 500 msec.

In some instances, the AC block is applied before the DC block, after the DC block, or interspersed within the DC block.

The electrodes can include conductive layers of aluminum, carbon, copper, gold, indium tin oxide, palladium, platinum, titanium, or hybrids thereof.

These normalized loop resistances thus can be used both as part of an algorithm that can correct for variations during the calculation of the analyte concentration and/or to trigger device failsafes that prevent displaying/reporting of the analyte concentration if variations in electrode conductivity exceed a predetermined threshold.

In another aspect, a scaling method is provided to compensate or correct for low or high Hct during a body fluid analysis for an analyte of interest. The method can include steps of applying to a body fluid sample an AC block in connection with at least one DC block, measuring AC and DC current responses, calculating a solution resistance ($R_{solution}$) from AC block signals and current responses, and multiplying DC current responses by $R_{solution}$ to obtain a compensated voltage drop that minimizes the influence of Hct on an estimated analyte concentration.

With respect to the AC block, it can be a plurality of low-amplitude signals applied sequentially or simultaneously in parallel. In some instances, the AC block includes at least two different low-amplitude signals. For example, the AC block can include two (2) segments at two (2) frequencies such as, for example, about 10 kHz or about 20 kHz followed by about 1 kHz or about 2 kHz. Alternatively, the AC block can have five (5) segments at four (4) frequencies such as, for example, about 10 kHz, about 20 kHz, about 10 kHz, about 2 kHz and about 1 kHz. Alternatively, the AC block can have four (4) segments at four (4) frequencies such as, for example, about 20 kHz, about 10 kHz, about 2 kHz and about 1 kHz. Alternatively, the AC block can have four (4) frequencies applied simultaneously at about 10 kHz, about 20 kHz, about 10 kHz, about 2 kHz and about 1 kHz. Alternately still, the AC block can have a multi-frequency excitation waveform that simultaneously applies desired low-amplitude AC signals.

In some instances, the AC block is applied for about 500 msec to about 1.5 sec. In other instances, the AC block is applied for about 100 msec to about 300 msec.

With respect to the DC block, it can include at least one (1) pulse to about ten (10) pulses at a potential that alternates between about 0 mV to about +450 mV. In some instances, the DC block is a single potential step from about 0 mV to about +450 mV, where the potential is maintained so that a decaying current response may be detected. That is, the DC block includes at least one excitation pulse and at least one recovery pulse, where the pulses alternate between about 0 mV to about +450 mV.

Regardless of the number of pulses, each DC pulse can be applied for about 50 msec to about 500 msec. In particular, each DC pulse at about +450 mV can be applied for about 250 msec, and each DC pulse at about 0 mV can be applied for about 500 msec.

In some instances, the AC block is applied before the DC block, after the DC block, or interspersed within the DC block.

The method also can include a step of constructing algorithms that incorporate a Hct-compensated voltage to thereby provide an estimated analyte concentration.

In another aspect, a scaling method is provided to compensate for Hct and/or temperature during a body fluid analysis for an analyte of interest. The method includes steps of applying to a body fluid sample an AC block in connection with at least one DC block, measuring AC and DC current responses, calculating admittance (Y) from at least one of the AC signals and responses, and dividing the DC current responses by the admittance (Y) to obtain a compensated current that minimizes the influence of Hct and/or temperature on the DC current and hence the analyte concentration.

With respect to the AC block, it can be a plurality of low-amplitude signals applied sequentially or simultaneously in parallel. In some instances, the AC block includes at least two different low-amplitude signals. For example, the AC block can include two (2) segments at two (2) frequencies such as, for example, about 10 kHz or about 20 kHz followed by about 1 kHz or about 2 kHz. Alternatively, the AC block can have five (5) segments at four (4) frequencies such as, for example, about 10 kHz, about 20 kHz, about 10 kHz, about 2 kHz and about 1 kHz. Alternatively, the AC block can have four (4) segments at four (4) frequencies such as, for example, about 20 kHz, about 10 kHz, about 2 kHz and about 1 kHz. Alternatively, the AC block can have four (4) frequencies applied simultaneously at about 10 kHz, about 20 kHz, about 10 kHz, about 2 kHz and about 1 kHz. Alternately still, the AC block can have a multi-frequency excitation waveform that simultaneously applies desired low-amplitude AC signals.

In some instances, the AC block is applied for about 500 msec to about 1.5 sec. In other instances, the AC block is applied for about 100 msec to about 300 msec.

With respect to the DC block, it can include at least one (1) pulse to about ten (10) pulses at a potential that alternates between about 0 mV to about +450 mV. In some instances, the DC block can be a single potential step from about 0 mV to about +450 mV, where the potential is maintained so that a decaying current response may be detected. That is, the DC block includes at least one excitation pulse and at least one recovery pulse, where the pulses alternate between about 0 mV to about +450 mV.

Regardless of the number of pulses, each DC pulse can be applied for about 50 msec to about 500 msec. For example, each DC pulse at +450 mV can be applied for about 250 msec, and each DC pulse at 0 mV can be applied for about 500 msec.

In some instances, the AC block is applied before the DC block, after the DC block, or interspersed within the DC block.

In some instances, the admittance (Y) is calculated at 20 kHz ($Y_{20}$).

The method also can include a step of constructing algorithms that incorporate the Hct- and/or temperature-compensated current to provide an estimated analyte concentration.

In another aspect, a related scaling method is provided to compensate for Hct and/or temperature during a body fluid analysis for an analyte of interest. The method includes steps of applying to a body fluid sample an AC block in connection with at least one DC block, measuring AC and DC current responses, calculating admittance (Y) to its optimal power from at least one of the AC signals and responses, and dividing the DC current responses by the powered admittance (Y) to obtain a compensated current that minimizes the influence of Hct and/or temperature on the DC current and hence the analyte concentration.

With respect to the AC block, it can be a plurality of low-amplitude signals applied sequentially or simultaneously in parallel. In some instances, the AC block includes at least two different low-amplitude signals. For example, the AC block can include two (2) segments at two (2) frequencies such as, for example, about 10 kHz or about 20 kHz followed by about 1 kHz or about 2 kHz. Alternatively, the AC block can have five (5) segments at four (4) frequencies such as, for example, about 10 kHz, about 20 kHz, about 10 kHz, about 2 kHz and about 1 kHz. Alternatively, the AC block can have four (4) segments at four (4) frequencies such as, for example, about 20 kHz, about 10 kHz, about 2 kHz and about 1 kHz. Alternatively, the AC block can have four (4) frequencies applied simultaneously at about 10 kHz, about 20 kHz, about 10 kHz, about 2 kHz and about 1 kHz. Alternately still, the AC block can have a multi-frequency excitation waveform that simultaneously applies desired low-amplitude AC signals.

In some instances, the AC block is applied for about 500 msec to about 1.5 sec. In other instances, the AC block is applied for about 100 msec to about 300 msec.

With respect to the DC block, it can include at least one (1) pulse to about ten (10) pulses at a potential that alternates between about 0 mV to about +450 mV. In some instances, the DC block can be a single potential step from about 0 mV to about +450 mV, where the potential is maintained so that a decaying current response may be detected. That is, the DC block includes at least one excitation pulse and at least one recovery pulse, where the pulses alternate between about 0 mV to about +450 mV.

Regardless of the number of pulses, each DC pulse can be applied for about 50 msec to about 500 msec. For example, each DC pulse at +450 mV can be applied for about 250 msec, and each DC pulse at 0 mV can be applied for about 500 msec.

In some instances, the AC block is applied before the DC block, after the DC block, or interspersed within the DC block.

The method also can include a step of constructing algorithms that incorporate the Hct- and/or temperature-compensated voltage to provide an estimated analyte concentration.

In view of the foregoing, devices, apparatuses and systems used in connection with body fluid analysis are provided that incorporate one or more of the scaling methods disclosed herein. These devices, apparatuses and systems can be used to determine concentration of analytes including, but not limited to, amino acids, antibodies, bacteria, carbohydrates, drugs, lipids, markers, nucleic acids, peptides, proteins, toxins, viruses and other analytes, as well as combinations thereof. In certain instances, the analyte is glucose.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
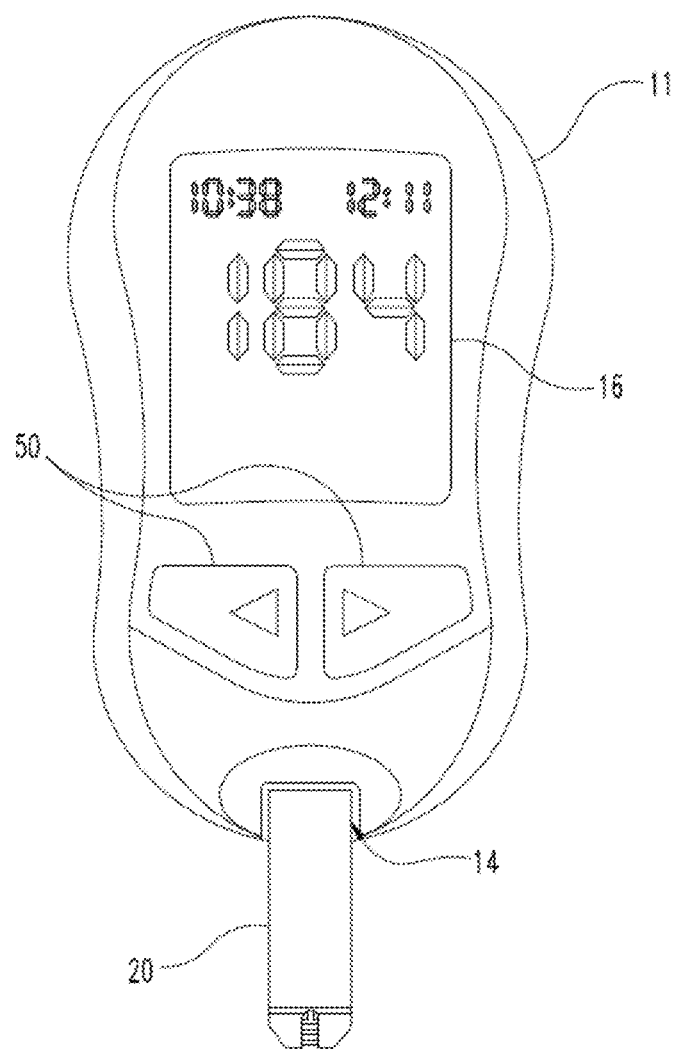
FIG. 1 shows an exemplary analyte measurement system including a meter and biosensor.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The methods, devices, apparatuses and systems now will be described more fully hereinafter with reference to the accompanying drawings, in which some, but not all embodiments of the inventive concept are shown. Indeed, the inventive concept may be embodied in many different forms and should not be construed as limited to the embodiments set forth herein; rather, these embodiments are provided so that this disclosure will satisfy applicable legal requirements.

Likewise, many modifications and other embodiments of the methods, devices, apparatuses and systems described herein will come to mind to one of skill in the art to which the disclosure pertains having the benefit of the teachings presented in the foregoing descriptions and the associated drawings. Therefore, it is to be understood that the inventive concept is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the present methods, devices, apparatuses and systems, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Overview

Scaling methods are disclosed herein that use response information derived from AC potentials to scale DC response data in a manner that reduces the impact of confounding variables on an analyte concentration. These scaling methods therefore can be used to reduce the effects of confounding variables such as Hct and/or temperature on observed DC current responses—before creating algorithms. Likewise, the scaling methods also can be used to reduce the effects of variations in electrode conductivity, particularly variations caused by variations in raw materials and non-uniform resistances among electrodes in an electrode system.

Advantageously, the scaling methods disclosed herein can be used in algorithms that deliver more accurate and reliable analyte concentration measurements and failsafes during the use of various electrochemical measurement methods including amperometry. If the failsafe is triggered, an analyte concentration measuring device, apparatus or system can be configured to deliver an error code or an error message rather than an inaccurate analyte concentration. For example, the failsafe could include direct messaging such as: "A conductive layer error in the biosensor was detected and thus an analyte concentration cannot be reported." This could result in a health care professional or user follow up to determine the cause and find a suitable device or biosensor that may not have this issue.

The scaling methods also can be applied before other electrochemical methods such as voltammetry or analysis of coulometric, potentiometric or voltammetric measurement data, in which current (or in this case, a scaled/compensated current) is summed to produce a charge (Q) collected during the period of an applied potential or series of potential pulses. Additional details regarding exemplary electrochemical measurement methods are disclosed in, for example, U.S. Pat. Nos. 4,008,448; 4,225,410; 4,233,029; 4,323,536; 4,891,319; 4,919,770; 4,963,814; 4,999,582; 4,999,632; 5,053,199; 5,108,564; 5,120,420; 5,122,244; 5,128,015; 5,243,516; 5,288,636; 5,352,351; 5,366,609; 5,385,846; 5,405,511; 5,413,690; 5,437,999; 5,438,271; 5,508,171; 5,526,111; 5,627,075; 5,628,890; 5,682,884; 5,727,548; 5,762,770; 5,858,691; 5,997,817; 6,004,441; 6,054,039; 6254736; 6,270,637; 6,645,368; 6,662,439; 7,073,246; 7,018,843; 7,018,848; 7,045,054; 7,115,362; 7,276,146; 7,276,147; 7,335,286; 7,338,639; 7,386,937; 7,390,667; 7,407,811; 7,429,865; 7,452,457; 7,488,601; 7,494,816; 7,545,148; 7,556,723; 7,569,126; 7,597,793; 7,638,033; 7,731,835; 7,751,864; 7,977,112; 7,981,363; 8,148,164; 8,298,828; 8,329,026; 8,377,707; and 8,420,404, as well as RE36268, RE42560, RE42924 and RE42953.

Advantageously, the methods described herein can be incorporated into SMBG devices, apparatuses and systems to reduce effects of Hct and/or temperature on a reported analyte concentration, such as a glucose concentration. Likewise, other methods described herein can be incorporated into SMBG devices, apparatuses and systems to reduce effects of variations of the electrical conductor or other raw material on a reported analyte concentration.

Moreover, these scaling methods can be implemented using advanced microprocessor-based algorithms and processes that result in dramatically improved system performance. These methods also offer flexibility and number of ways to create algorithms that can achieve improved performance such as 10/10 performance. As used herein, "10/10 performance" means that a measured bG value is within about ±10% of the actual bG value for bG concentrations >100 mg/dL, and within ±10 mg/dL of the actual bG value for bG concentrations <100 mg/dL.

Details regarding additional electrochemical measurement methods that may be useful in performing the methods disclosed herein can be found in the following co-filed and co-pending patent applications titled: "METHODS OF ELECTROCHEMICALLY MEASURING AN ANALYTE WITH A TEST SEQUENCE HAVING A PULSED DC BLOCK AS WELL AS DEVICES, APPARATUSES AND SYSTEMS INCORPORATING THE SAME" (Int'l Patent Application No. PCT/EP2014/054965 and U.S. patent application Ser. No. 14/851,621); "METHODS OF FAILSAFING ELECTROCHEMICAL MEASUREMENTS OF AN ANALYTE AS WELL AS DEVICES, APPARATUSES AND SYSTEMS INCORPORATING THE SAME" (Int'l Patent Application No. PCT/EP2014/054955 and US patent application Ser. No. 14/851,807); "METHODS OF USING INFORMATION FROM RECOVERY PULSES IN ELECTROCHEMICAL ANALYTE MEASUREMENTS AS WELL AS DEVICES, APPARATUSES AND SYSTEMS INCORPORATING THE SAME" (Int'l Patent Application No. PCT/EP2014/054943 and U.S. patent application Ser. No. 14/851,944); "DESCRIPTOR-BASED METHODS OF ELECTROCHEMICALLY MEASURING AN ANALYTE AS WELL AS DEVICES, APPARATUSES AND SYSTEMS INCOPORATING THE SAME" (Int'l Patent Application No. PCT/EP2014/054956 and U.S. patent application Ser. No. 14/852,044); and "METHODS OF DETECTING HIGH ANTIOXIDANT LEVELS DURING ELECTROCHEMICAL MEASUREMENTS AND FAILSAFING AN ANALYTE CONCENTRATION THEREFROM AS WELL AS DEVICES, APPARATUSES AND SYSTEMS INCORPORTING THE SAME" (Int'l Patent Application No. PCT/EP2014/054962 and U.S. patent application Ser. No. 14/852,114).

Analyte Measurement Devices, Apparatuses and Systems

Prior to, and in connection with, describing the inventive measurement methods, FIG. 1 shows an exemplary analyte measurement system including a device such as a test meter 11 operatively coupled with an electrochemical biosensor 20 (also known as a test element). Meter 11 and biosensor 20 are operable to determine concentration of one or more analytes in a fluidic sample provided to the biosensor 20. In some instances, the sample may be a body fluid sample such as, for example, whole blood, plasma, serum, urine or saliva. In other instances, the fluidic sample may be another type of sample to be tested for the presence or concentration of one or more electrochemically reactive analyte(s) such as an aqueous environmental sample.

In FIG. 1, the biosensor 20 is a single use test strip removably inserted into a connection terminal 14 of meter 11. In some instances, biosensor 20 is configured as a blood glucose test element and includes features and functionalities for electrochemically measuring glucose. In other instances, biosensor 20 is configured to electrochemically measure one or more other analytes such as, for example, amino acids, antibodies, bacteria, carbohydrates, drugs, lipids, markers, nucleic acids, peptides, proteins, toxins, viruses, and other analytes.

Meter 11 includes an electronic display 16 that is used to display various types of information to the user including analyte concentration(s) or other test results, and user interface 50 for receiving user input. Meter 11 further includes a microcontroller and associated test signal generating and measuring circuitry (not shown) that are operable to generate a test signal, to apply the signal to the biosensor 20, and to measure one or more responses of the biosensor 20 to the test signal. In some instances, meter 11 can be configured as a blood glucose measurement meter and includes features and functionalities of the ACCU-CHEK® AVIVA® meter as described in the booklet "Accu-Chek® Aviva Blood Glucose Meter Owner's Booklet" (2007), portions of which are disclosed in U.S. Pat. No. 6,645,368. In other instances, meter 11 can be configured to electrochemically measure one or more other analytes such as, for example, amino acids, antibodies, bacteria, carbohydrates, drugs, lipids, markers, nucleic acids, proteins, peptides, toxins, viruses, and other analytes. Additional details regarding exemplary meters configured for use with electrochemical measurement methods are disclosed in, for example, U.S. Pat. Nos. 4,720,372; 4,963,814; 4,999,582; 4,999,632; 5,243,516; 5,282,950; 5,366,609; 5,371,687; 5,379,214; 5,405,511; 5,438,271; 5,594,906; 6,134,504; 6,144,922; 6,413,213; 6,425,863; 6,635,167; 6,645,368; 6,787,109; 6,927,749; 6,945,955; 7,208,119; 7,291,107; 7,347,973; 7,569,126; 7,601,299; 7,638,095 and 8,431,408.

One of skill in the art understands that the scaling methods described herein can be used in other measurement devices, apparatuses, systems and environments such as, for example, hospital test systems, laboratory test systems and others.

It shall be understood that the biosensor and meter can include additional and/or alternate attributes and features in addition to or instead of those shown in FIG. 1. For example, the biosensor can be in the form of a single use, disposable electrochemical test strip having a substantially rectangular shape. It shall be appreciated that the biosensors can include different forms such as, for example, test strips of different configurations, dimensions or shapes, non-strip test elements, disposable test elements, reusable test elements, micro-arrays, lab-on-chip devices, bio-chips, bio-discs, bio-cds or other test elements.

Figure 2:
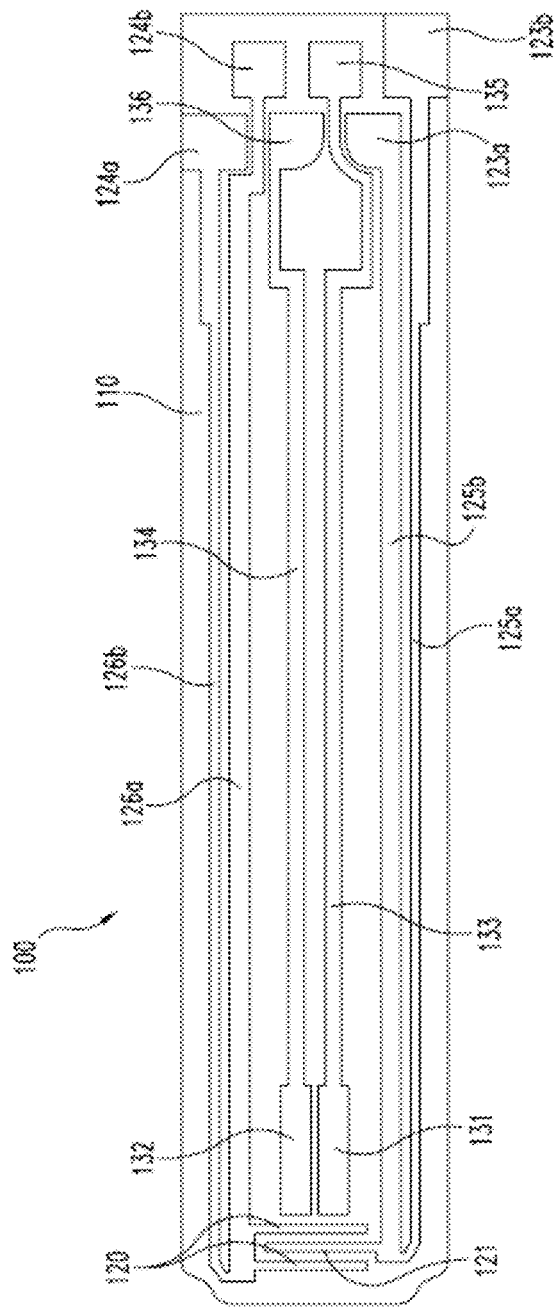
FIG. 2 shows a top view of an exemplary biosensor electrode system for electrochemically determining an analyte concentration in a fluidic sample.

FIG. 2 shows a more detailed view of an exemplary biosensor 100 including a substrate 110 and an arrangement of electrically conductive material provided on the substrate 110. The substrate 110 can be a polyethylene terephthalate ("PET"). The substrate 110 also may include other materials including, for example, polyesters or other polymeric or thermoplastic materials among others. Conductive material on substrate 110 includes a material that can be provided on the substrate to define electrodes and/or code patterns, such as gold or a gold alloy. Additional materials that may be used include, but are not limited to, platinum, palladium, iridium, or alloys thereof.

Also shown in FIG. 2 is an exemplary pattern of conductive material that may be useful for biosensors provided for an electrochemical fluid sample analysis system. Other biosensors may include a variety of other conductive patterns useful in performing electrochemical analyte measurement. The electrically conductive material typically is arranged on substrate 110 to provide a number of electrically conductive pathways. Particular arrangements of electrically conductive material, such as the arrangement illustrated in FIG. 2, may be provided using a number of techniques including chemical vapor deposition, laser ablation, lamination, screen-printing, photolithography, and combinations of these and other techniques. One illustrated electrically conductive pathway includes a working electrode 121, working electrode contact pads 123a and 123b and conductive trace portions 125a and 125b that extend between and electrically couple working electrode 121 and working electrode contact pads 123a and 123b.

An alternative electrically conductive pathway shown in FIG. 2 includes counter electrode 120 (illustrated as comprising dual prongs), counter electrode contact pads 124a and 124b, and conductive trace portions 126a and 126b that extend between and electrically couple counter electrode 120 and counter electrode contact pads 124a and 124b.

A further electrically conductive pathway shown in FIG. 2 includes sample sufficiency electrode 131, sample sufficiency contact pad 135 and conductive trace portion 133 that extends between and electrically couples sample sufficiency electrode 131 and sample sufficiency contact pad 135. Another illustrated conductive pathway includes sample sufficiency electrode 132, sample sufficiency contact pad 136 and conductive trace portion 134 which extends between and electrically couples sample sufficiency electrode 132 and sample sufficiency contact pad 136. The sample sufficiency electrodes 131 and 132 may be used to implement a number of techniques for determining the sufficiency of a test sample provided to test element 100.

During a test operation involving biosensor 100, working electrode contact pads 123a and 123b may be coupled to working electrode terminals of a meter, counter electrode contact pads 124a and 124b may be coupled to counter electrode terminals of a meter, and sample sufficiency contact pads 135 and 136 may be coupled to respective sample detect terminals of a meter. A fluidic sample to be analyzed may be provided to biosensor 100, for example, by introducing the fluidic sample into a sample chamber. The meter and biosensor 100 may be used to check alignment of the test element relative to the meter, to perform failsafe or error checking functions, for example, verifying the integrity of conductive pathways by testing for expected electrical characteristics between working electrode contact pads 123a and 123b or counter electrode contact pads 124a and 124b, to perform fill detection and sample sufficiency detection functions utilizing pads 135 and 136, and to perform electrochemical analysis functions such blood glucose concentration measurement or detection or measurement of other analytes.

Additional details regarding exemplary biosensors configured for use with electrochemical measurement methods are disclosed in, for example, U.S. Pat. Nos. 5,694,932; 5,762,770; 5,948,695; 5,975,153; 5,997,817; 6,001,239; 6,025,203; 6,162,639; 6,245,215; 6,271,045; 6,319,719; 6,406,672; 6,413,395; 6,428,664; 6,447,657; 6,451,264; 6,455,324; 6,488,828; 6,506,575; 6,540,890; 6,562,210; 6,582,573; 6,592,815; 6,627,057; 6,638,772; 6,755,949; 6,767,440; 6,780,296; 6,780,651; 6,814,843; 6,814,844; 6,858,433; 6,866,758; 7,008,799; 7,063,774; 7,238,534; 7,473,398; 7,476,827; 7,479,211; 7,510,643; 7,727,467; 7,780,827; 7,820,451; 7,867,369; 7,892,849; 8,180,423; 8,298,401; 8,329,026, as well as RE42560, RE42924 and RE42953.

Scaling Methods

As noted above, the scaling methods described herein are based upon an inventive concept that includes using information derived from AC signals and current responses to scale amperometric data in a manner that attenuates, minimizes or reduces the impact of confounding variables before constructing descriptors and algorithms that provide analyte concentration. Specifically, the scaling methods use information derived from AC current responses to compensate or correct for confounding variables such as Hct and/or temperature, and variations of the electrical conductor raw material on a reported analyte concentration.

Figure 3A:
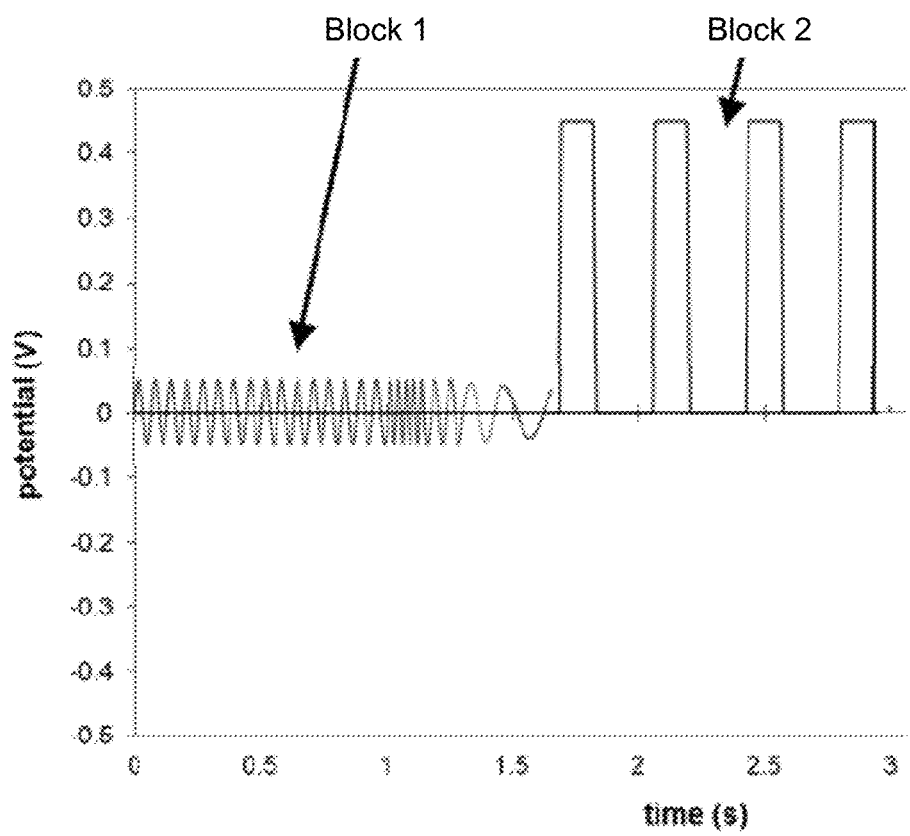
FIGS. 3A-C show exemplary test signals that may be employed by an analyte testing device, apparatus or system.
Figure 3B:
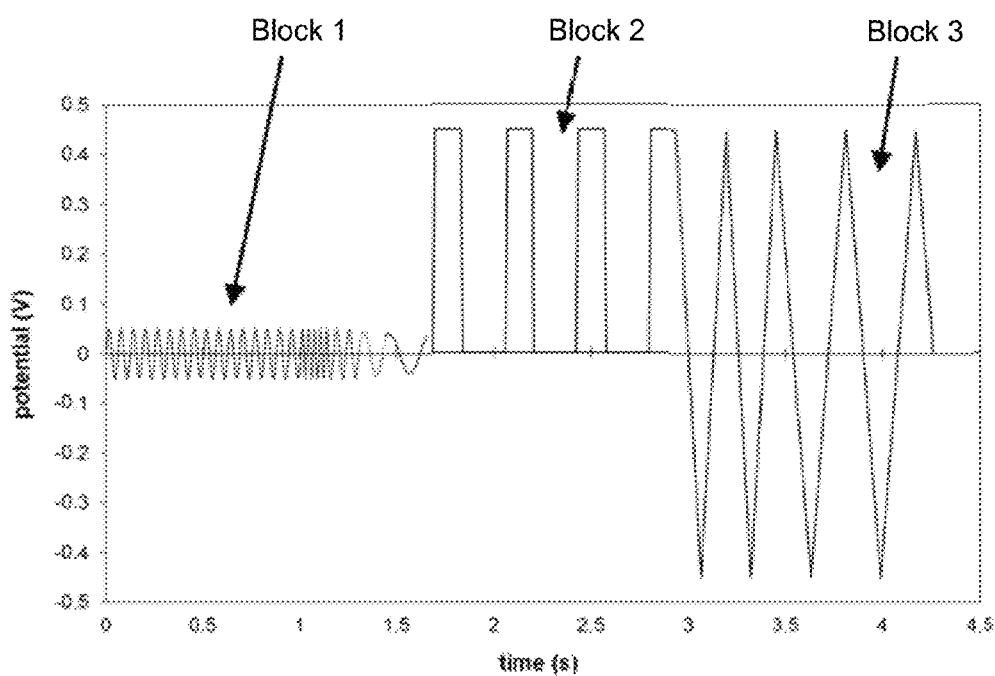
Figure 3C:
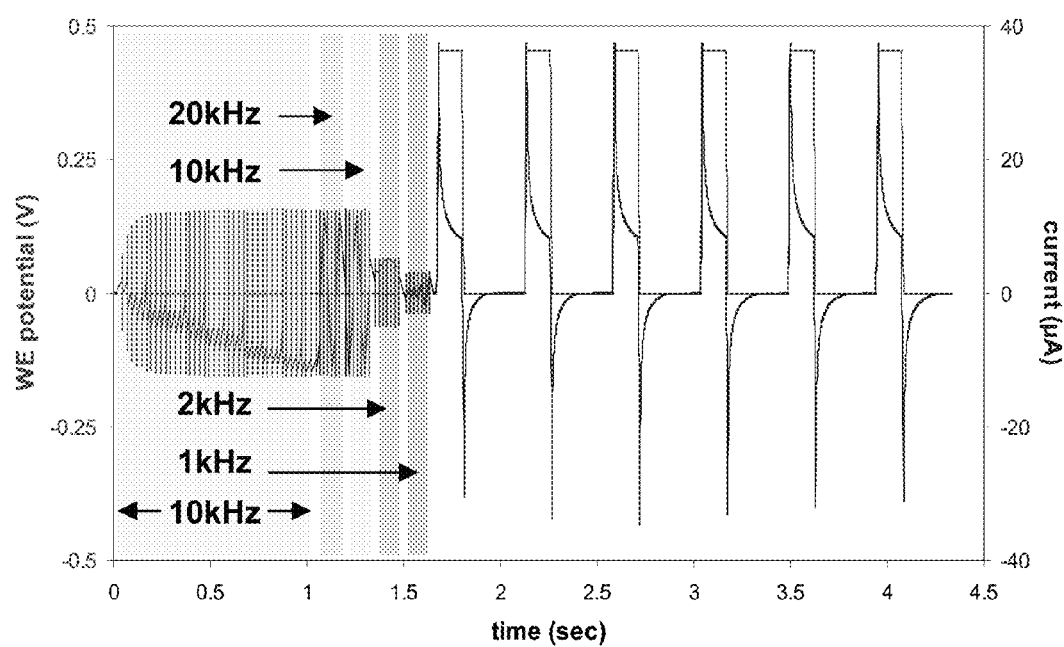

Some steps in common among the methods are applying to a fluidic sample such as body fluid an AC block of low-amplitude signals in connection with a DC block and measuring current responses thereto. FIGS. 3A-C show exemplary test sequences that may be used in connection with SMBG and other test systems. As shown in FIGS. 3A-B, the test sequence can include one or more blocks of AC and or DC potentials. For example, the test sequence can include an AC block of low-amplitude signals followed by a controlled DC block such as: (1) an AC block of a plurality of segments at different frequencies; and (2) a DC block of short-duration (e.g., about 50-500 msec) about +450-mV pulses separated by similarly short-duration (e.g., about 50-500 msec) recovery pulses, during which a closed circuit about 0-mV recovery potential is applied.

With respect to the AC block, it can include a plurality of AC segments such as, for example, from about 2 segments to about 10 segments, from about 3 segments to about 9 segments, from about 4 segments to about 8 segments, from about 5 segments to about 7 segments, or about 6 segments. In other instances, the AC block can include about 2 segments, about 3 segments, about 4 segments, about 5 segments, about 6 segments, about 7 segments, about 8 segments, about 9 segments, or about 10 segments. In still other instances, the AC block can have more than 10 segments, that is, about 15 segments, about 20 segments, or about 25 segments. In yet other instances, the AC block can include 1 segment, where the segment has multiple low-frequency AC signals applied simultaneously.

One of skill in the art understands that the number of AC segments will be limited by the complexity of the response, the associated frequency range and time available to perform the measurements. Higher frequencies generally require high bandwidth electronics and faster sampling, whereas lower frequencies take longer and typically are noisier. The maximum number of segments therefore will be a compromise of these parameters, choosing the minimum count and frequency span needed to discriminate the sample and environmental and/or confounding factors of interest.

As used herein, "about" means within a statistically meaningful range of a value or values such as a stated concentration, length, molecular weight, pH, potential, time frame, temperature, voltage or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The frequency of each signal in each segment of the AC block can be from about 1 kHz to about 20 kHz, from about 2 kHz to about 19 kHz, from about 3 kHz to about 18 kHz, from about 4 kHz to about 17 kHz, from about 5 kHz to about 16 kHz, from about 6 kHz to about 15 kHz, from about 7 kHz to about 14 kHz, from about 8 kHz to about 13 kHz, from about 9 kHz to about 12 kHz or from about 10 kHz to about 11 kHz. In other instances, the frequency of each segment in the AC block can be about 1 kHz, about 2 kHz, about 3 kHz, about 4 kHz, about 5 kHz, about 6 kHz, about 7 kHz, about 8 kHz, about 9 kHz, about 10 kHz, about 11 kHz, about 12 kHz, about 13 kHz, about 14 kHz, about 15 kHz, about 16 kHz, about 17 kHz, about 18 kHz, about 19 kHz, or about 20 kHz. In still other instances, the frequency of each signal in each segment of the AC block can be more than 20 kHz, that is, about 30 kHz, about 40 kHz, or about 50 kHz. In some instances, one or more of the segments can have the same frequency, whereas in other instances each segment has a distinct frequency from the other segments. Four frequencies, however, generally is adequate. The exact frequencies employed can be readily generated by simple integer division of a measurement system clock's maximum frequency.

A maximum frequency limit for a signal in a segment of the AC block, however, can be up to about 100 kHz for an inexpensive, battery-powered handheld instrument. Beyond that, the increasing demands on analog bandwidth, sampling rate, storage and processing speed quickly add up, while the imaginary portion of a typical biosensor response becomes increasingly smaller with frequency. Lower frequencies have longer periods and take longer times to sample with comparable accuracy.

The AC block typically includes at least two different low-amplitude signals. For example, the AC block can include two (2) segments at two (2) frequencies such as, for example, about 10 kHz or about 20 kHz followed by about 1 kHz or about 2 kHz. In other instances, the AC block includes a plurality of low-amplitude signals. For example, the AC block can have five (5) segments at four (4) frequencies such as, for example, about 10 kHz, about 20 kHz, about 10 kHz, about 2 kHz and about 1 kHz. Alternatively, the AC block can have four (4) segments at four (4) frequencies such as, for example, about 20 kHz, about 10 kHz, about 2 kHz and about 1 kHz. Alternatively, the AC block can have four (4) frequencies applied simultaneously at about 10 kHz, about 20 kHz, about 10 kHz, about 2 kHz and about 1 kHz. Alternately still, the AC block can have a multi-frequency excitation waveform that simultaneously applies the desired low-amplitude AC signals. The AC frequencies may be applied sequentially, or combined and applied simultaneously and analyzed via Fourier Transform.

The block of low-amplitude AC signals can be applied for about 500 msec to about 1.5 sec, about 600 msec to about 1.25 sec, about 700 msec to about 1000 msec, or about 800 msec to about 900 msec. Alternatively, the block of low-amplitude AC signals can be applied for about 500 msec, about 600 msec, about 700 msec, about 800 msec, about 900 msec, about 1000 msec, about 1.25 sec or about 1.5 sec. In particular, the block of low-amplitude AC signals can be applied for about 100 msec to about 300 msec.

One of skill in the art, however, understands that the number, frequency, duration and order of the AC segments can be varied.

AC current response information can be obtained at any time during a test sequence. Impedance results at lower frequencies may be influenced by analyte concentration if obtained after an electrochemical cell is DC polarized. In some instances, a series of AC current response measurements can be obtained early in the test sequence. Measurements taken shortly after a fluidic sample is applied to a biosensor will be influenced by diffusion, temperature and reagent solubility. In other instances, the AC response current measurements can be obtained at a sufficient time after an adequate sample has been applied to allow the response to stabilize, and avoid the transient response in the first second. Likewise, response current measurements can be made at one or more frequencies. Due to their capacitive nature, multiple AC measurements separated by a frequency octave or decade may offer different sensitivities or easier manipulation.

Additional details regarding exemplary AC blocks in electrochemical measurement methods are disclosed in, for example, U.S. Pat. Nos. 7,338,639; 7,390,667; 7,407,811; 7,417,811; 7,452,457; 7,488,601; 7,494,816; 7,597,793; 7,638,033; 7,751,864; 7,977,112; 7,981,363; 8,148,164; 8,298,828; 8,377,707 and 8,420,404.

With respect to the DC block, it can include a plurality of pulses such as, for example, from about 2 pulses to about 10 pulses, from about 3 pulses to about 9 pulses, from about 4 pulses to about 8 pulses, from about 5 pulses to about 7 pulses, or about 6 pulses. In other instances, the DC block can include about 2 pulses, about 3 pulses, about 4 pulses, about 5 pulses, about 6 pulses, about 7 pulses, about 8 pulses, about 9 pulses, or about 10 pulses. In still other instances, the DC block can have more than 10 pulses, that is, about 15 pulses, about 20 pulses, or about 25 pulses. As used herein, "pulse" means at least one excitation and one recovery period.

The DC block typically includes a constantly applied potential difference that alternates between about 0 mV and about +450 mV potential difference, or other slowly time-varying potential difference that can be analyzed by traditional DC electrochemical methods. One of skill in the art, however, understands that the range for the applied potential difference can, and will, vary depending upon the analyte and reagent chemistry used. As such, excitation pulse potential can be greater-than, less-than or equal to about +450 mV. Examples of excitation potentials include, but are not limited to, 50 mV, 75 mV, 100 mV, 125 mV, 150 mV, 175 mV, 200 mV, 225 mV, 250 mV, 275 mV, 300 mV, 325 mV, 350 mV, 375 mV, 400 mV, 425 mV, 450 mV, 475 mV, 500 mV, 525 mV, 550 mV, 575 mV, 600 mV, 625 mV, 650 mV, 675 mV, 700 mV, 725 mV. 750 mV, 775 mV, 800 mV, 825 mV, 850 mV, 875 mV, 900 mV, 925 mV, 950 mV, 975 mV or 1000 mV.

Regardless of the number, each DC pulse can be applied for about 50 msec to about 500 msec, about 60 msec to about 450 msec, about 70 msec to about 400 msec, about 80 msec to about 350 msec, about 90 msec to about 300 msec, about 100 msec to about 250 msec, about 150 msec to about 200 msec, or about 175 msec. Alternatively, each pulse can be applied for about 50 msec, about 60 msec, about 70 msec, about 80 msec, about 90 msec, about 100 msec, about 125 msec, about 150 msec, about 175 msec, about 200 msec, about 225 msec, about 250 msec, about 275 msec, about 300 msec, about 325 msec, about 350 msec, about 375 msec, about 400 msec, about 425 msec, about 450 msec, about 475 msec or about 500 msec. In particular, each DC pulse at +450 mV can be applied for about 250 msec, and each DC pulse at 0 mV can be applied for about 500 msec. Alternatively still, each pulse can be applied for less than about 50 msec or more than about 500 msec.

Generally, the ramp rate of each DC pulse is selected to provide about 50% or greater reduction in peak current relative to the peak current provided by a nearly ideal potential transition. In some instances, each pulse can have the same ramp rate. In other instances, some pulses can have the same ramp rate and other pulses can have a different ramp rate. In still other instances, each pulse has its own ramp rate. For example, effective ramp rates can be from about 5 mV/msec to about 75 mV/msec or from about 10 mV/msec to about 50 mV/msec, 15 mV/msec to about 25 mV/msec, or about 20 mV/msec. Alternatively, the ramp rate can be about 5 mV/msec, about 10 mV/msec, about 15 mV/msec, about 20 mV/msec, about 25 mV/msec, about 30 mV/msec, about 35 mV/msec, about 40 mV/msec, about 45 mV/msec, about 50 mV/msec, about 55 mV/msec, about 60 mV/msec, about 65 mV/msec, about 70 mV/msec, or about 75 mV/msec. In particular, the ramp rate can be from about 40 mV/msec to about 50 mV/msec.

Like the AC block, one of skill in the art understands that the number, potential, duration and order of the DC pulses can be varied.

AC and/or DC current response information is collected from the test sequence and includes current responses to the AC and DC blocks. In some instances, the current response information can be collected at an A/D sampling rate for DC and AC measurements to simplify the system design, including a single shared signal path for AC and DC measurements. Common digital audio sampling rates range include, but are not limited to, from about 44.1 kHz to about 192 kHz. A/D converters in this range are readily available from variety of commercial semiconductor suppliers.

A more detailed test sequence is shown in FIG. 3C, where one trace illustrates the applied DC potential, and the other trace illustrates the AC and DC current responses, respectively. In this example, the applied DC potential can be fixed at about 0 mV between pulses to provide a recovery pulse, thus making it a generally continuous excitation waveform. This is in contrast to a test sequence from known techniques that prescribe the use of an open circuit between positive DC pulses, thereby excluding the possibility of collecting and analyzing the current between positive pulses.

As used herein, "recovery pulse" means a zero-potential pulse (e.g., about −10 mV to about +10 mV) applied for an adequately long recovery period in which the electrochemical reaction with the analyte of interested (e.g., glucose) is turned "off," thereby allowing the system to return to a fixed starting point before subsequent interrogation with another positive DC pulse.

In a first exemplary scaling method (i.e., the "$R_{solution}$" method), high-frequency, low amplitude AC current responses can be used to determine $R_{solution}$ through a classical Randles circuit model, which then can be used to scale the DC current responses. $R_{solution}$ scaling reduces the impact of high and low Hct levels. This method also makes it possible to use the transformed data to build algorithms with linear form, giving rise to the possibility of simplifying algorithm complexity.

Figure 4:
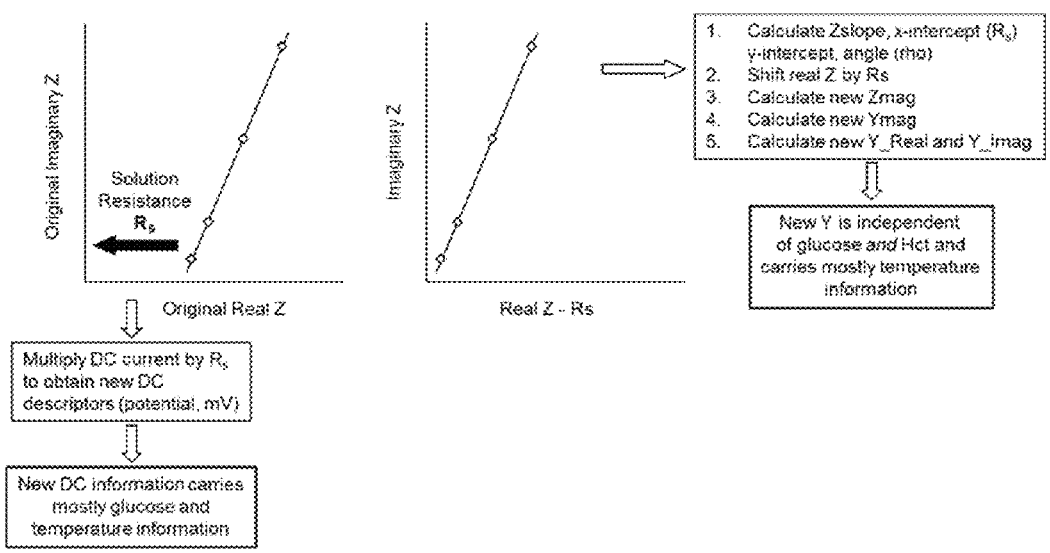
FIG. 4 shows an exemplary scaling method.

FIG. 4 shows an example of the first scaling method based upon an analysis of AC response information using a Nyquist plot. The AC measurements described above in connection with FIG. 3C produce complex impedance (Z) values that are close to linear; however, there is a significant x-intercept. Assuming a classic Randles circuit model, the scaling method uses the x-intercept (extrapolated real impedance) from a linear fit of four, complex AC values as an estimate of $R_{solution}$, which is strongly influenced by the Hct and salt content of the sample.

The calculated $R_{solution}$ for each sample then can be used to create compensated AC and DC values. For example, the DC current response values (in units of nA) can be directly multiplied by $R_{solution}$ to obtain a compensated voltage drop (in units of mV). This greatly minimizes the influence of Hct on the DC signal, leaving glucose as well as temperature effects.

The slope of the fitted impedance values, or the angle (with respect to origin), for the AC block also is descriptive of the sample. Such AC information can be calculated by subtracting $R_{solution}$ from the actual real impedance, and then calculating new impedance magnitudes for each frequency. The impedance magnitudes can be converted to admittance (Y) magnitudes, and real and imaginary admittance values and corresponding new angles can then be calculated.

This AC information also is characteristic of the sample and can be combined with $R_{solution}$-scaled/compensated DC values to produce various algorithms. Interestingly, these scaled/compensated admittance values are independent of glucose and Hct effects, and predominantly describe temperature.

In a second exemplary method (i.e., the "Factor" scaling method), the AC current responses can be used as a scaling factor of DC current responses to cancel out or largely remove the Hct and/or temperature impact on DC signal, which is the main contributor of predicting glucose value.

In a third exemplary method (i.e., the "Power" scaling method), which is related to the Factor scaling method, a power can be applied to the AC current responses to fine-tune the scaling.

In a fourth exemplary method (i.e., the "$R_{conductor}$" scaling method), at least two loop resistances from an electrode system of a biosensor can be measured and then normalized by dividing each of the loop resistances by its own constant, respectively. The lowest of the normalized loop resistances then can be incorporated into an analyte concentration algorithm or a failsafe calculation. Each constant can be obtained by taking a median of the respective loop resistances measured from a test batch or lot.

The $R_{conductor}$ scaling method takes into account non-uniform resistances in the electrode system that result from, for example, raw material and manufacturing variances, scratches or cracks that can occur post-manufacturing, and even contact resistance changes.

EXAMPLES

The inventive concept will be more fully understood upon consideration of the following non-limiting examples, which are offered for purposes of illustration, not limitation.

Example 1

The $R_{solution}$ Scaling Method

Figure 5A:
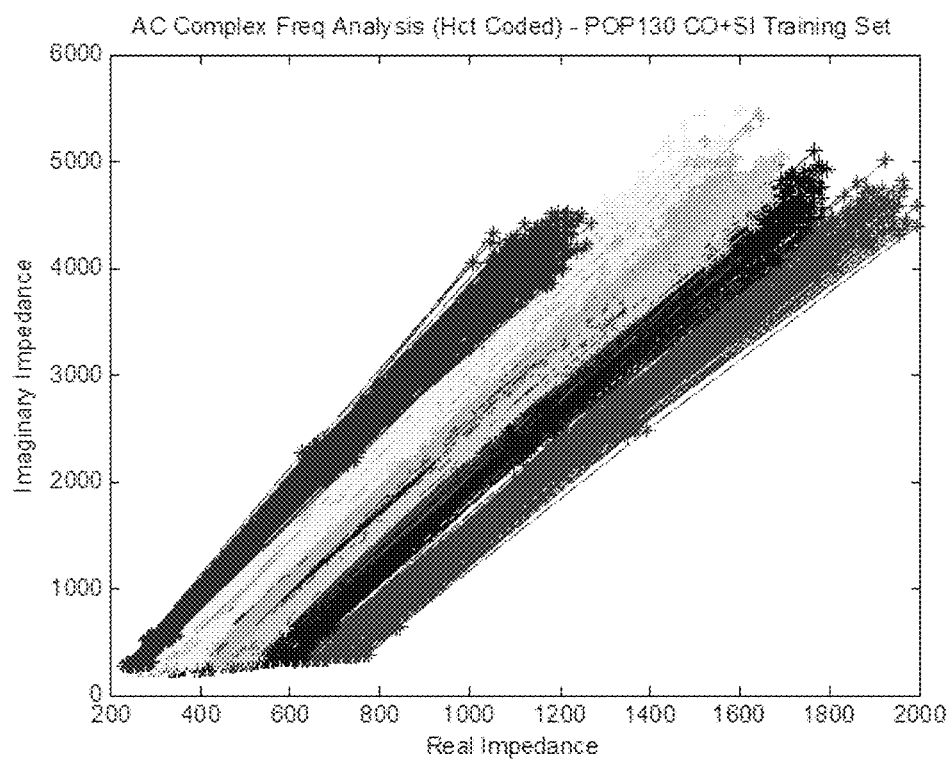
FIGS. 5A-C are graphs showing results of an AC frequency analysis performed in connection with the exemplary scaling process of FIG. 4.
Figure 5B:
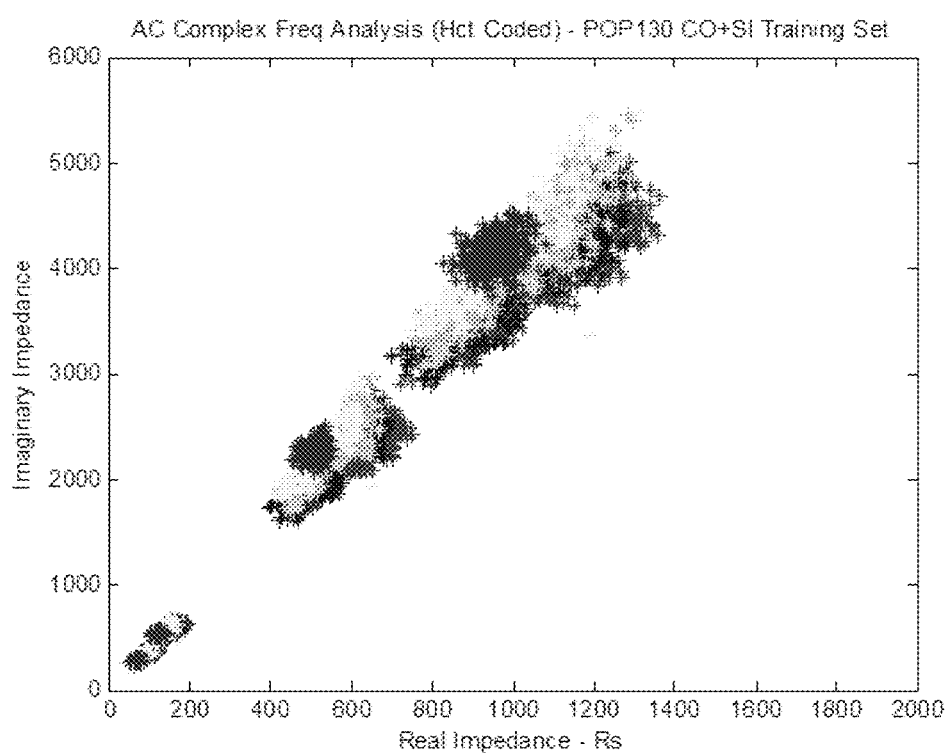
Figure 5C:
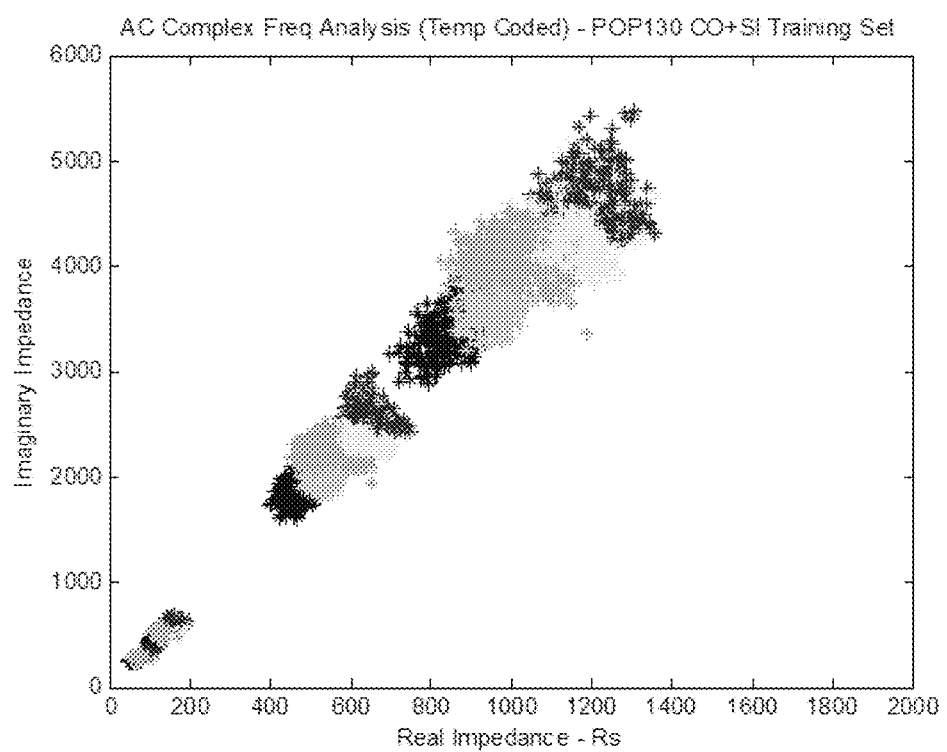

This example shows results of the first exemplary scaling method as shown in FIGS. 5A-C, which depict Nyquist plots for a large dataset of glycolized venous blood samples produced with an experimental design in which glucose, Hct and temperature were systematically co-varied. The dataset also contained spiked plasma samples at three different salt levels. These results are from a large dataset of glycolized venous blood samples with co-varied glucose, Hct and temperature levels combined with nominal spiked plasma samples containing different levels of salt.

FIG. 5A shows complex AC responses in spectral order and represents low-to-high Hct levels. One set of responses corresponds to the plasma samples with different salt concentrations. Using the methods described above and shown in FIG. 4, an estimate of $R_{solution}$ was obtained for each sample and then subtracted from each of the observed values of real impedance.

The $R_{solution}$ compensated results are shown in the plots of FIGS. 5B-C. Both plots have identical values; however, the plot of FIG. 5B is in spectral order by Hct, and the plot of FIG. 5C is in spectral order by temperature. FIG. 5B shows evidence of residual Hct sorting, but all of the samples look much more similar than in the plot above. In contrast, the plot of FIG. 5C shows that temperature is a more dominant factor. Interestingly, no glucose information is encoded by the plots of FIGS. 5A-C.

Figure 6A:
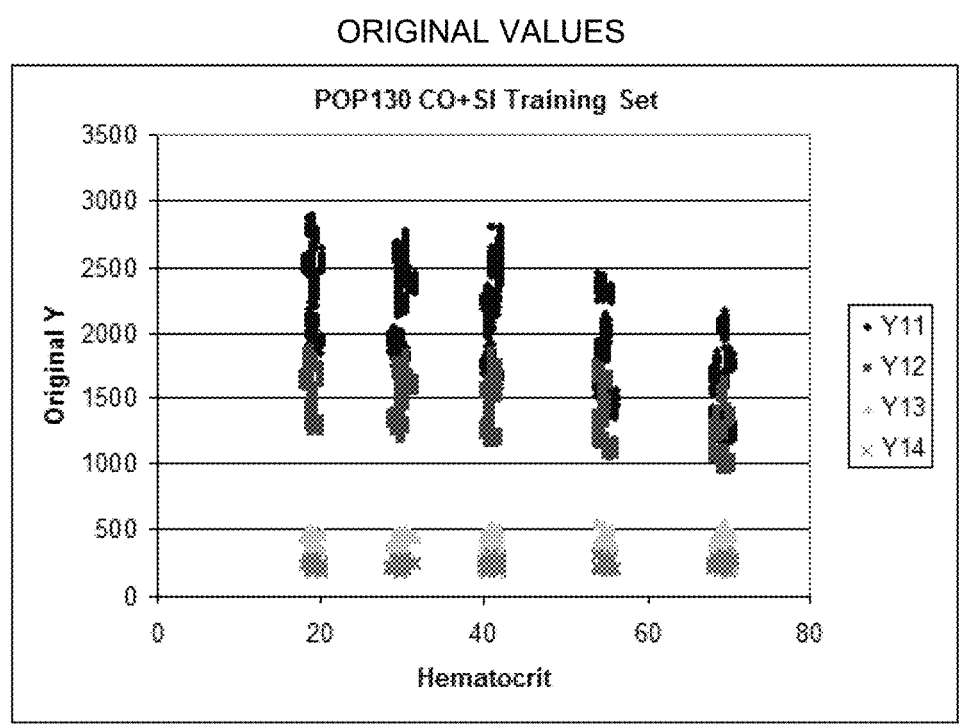
FIGS. 6A-F are graphs showing effects of $R_{solution}$ scaling on AC and DC data performed in connection with the exemplary scaling process of FIG. 4.
Figure 6B:
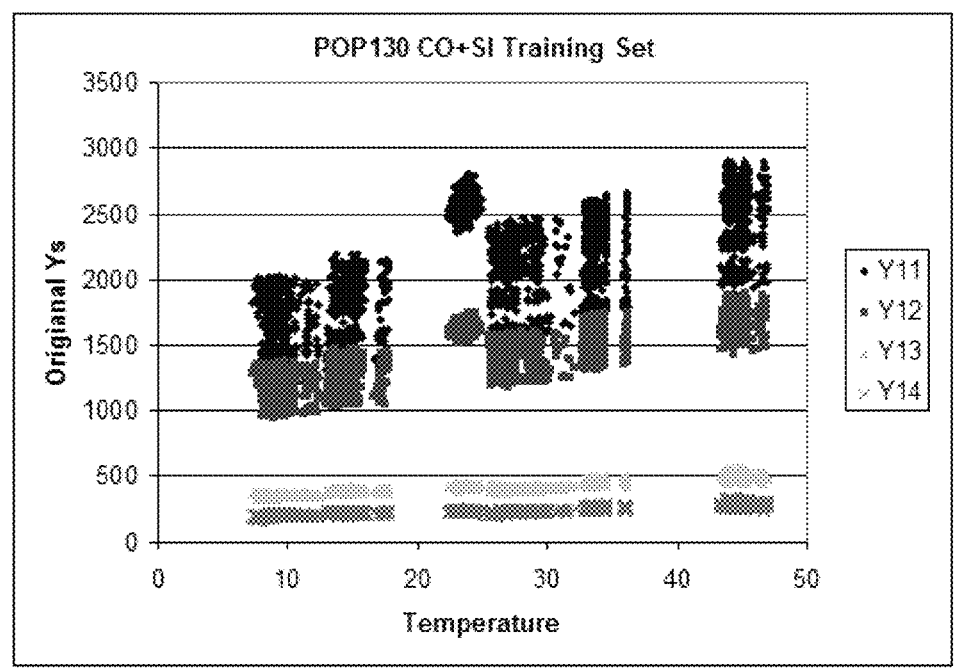

The results of the first exemplary scaling method also are shown in FIGS. 6A-F. The plots of FIGS. 6A-B show that the measured admittance (Y) values at each frequency are dependent upon both Hct and temperature, respectively. As noted in FIG. 6B, the clusters of data points with elevated admittance values correspond to plasma samples with elevated salt levels. The effects of compensating by $R_{solution}$ can clearly be seen in the lower and middle plots, in which the new admittance values are shown as a function of Hct and temperature, respectively.

Figure 6C:
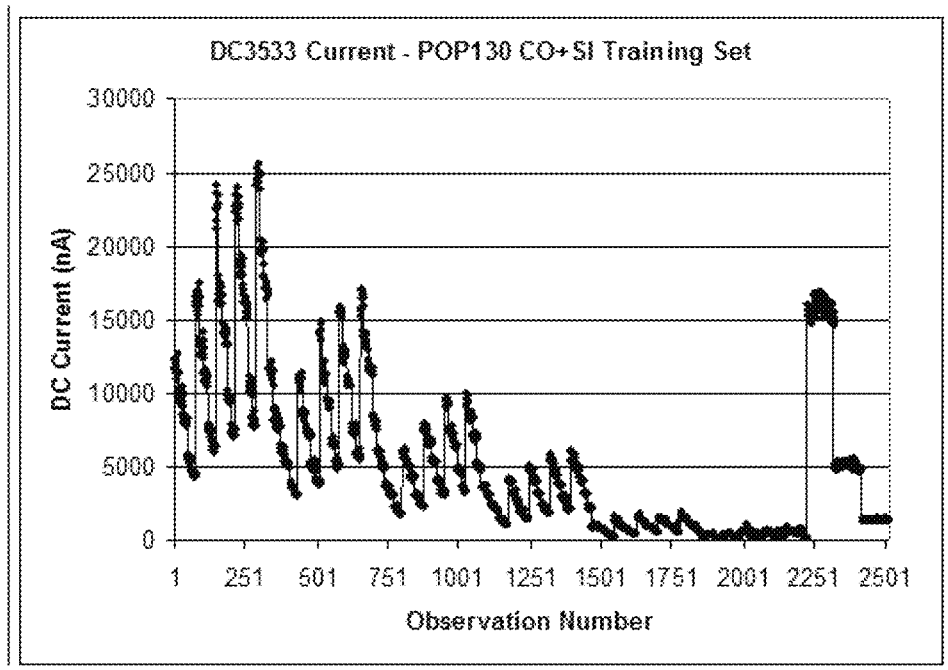
Figure 6D:
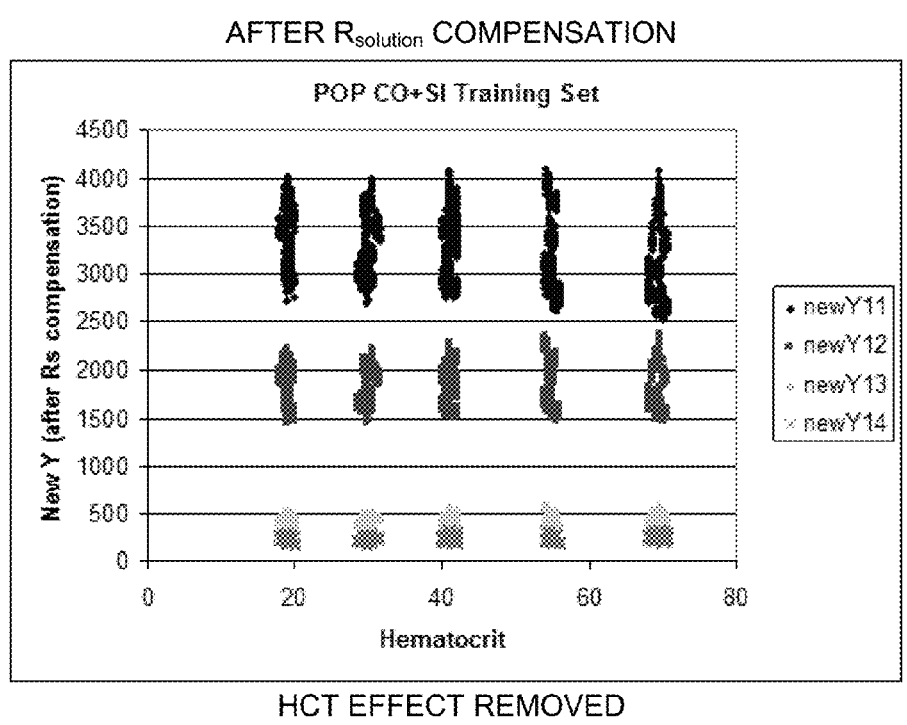
Figure 6E:
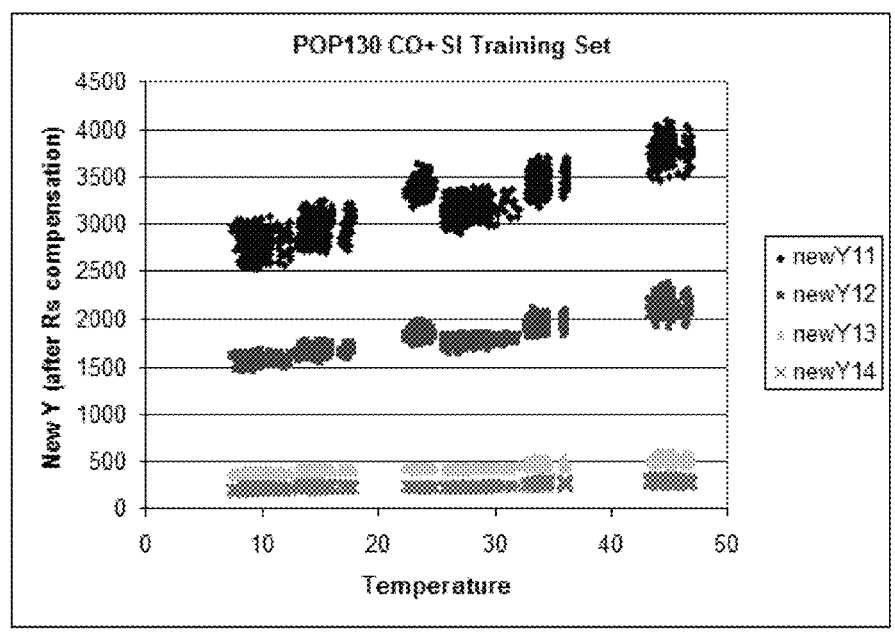
Figure 6F:
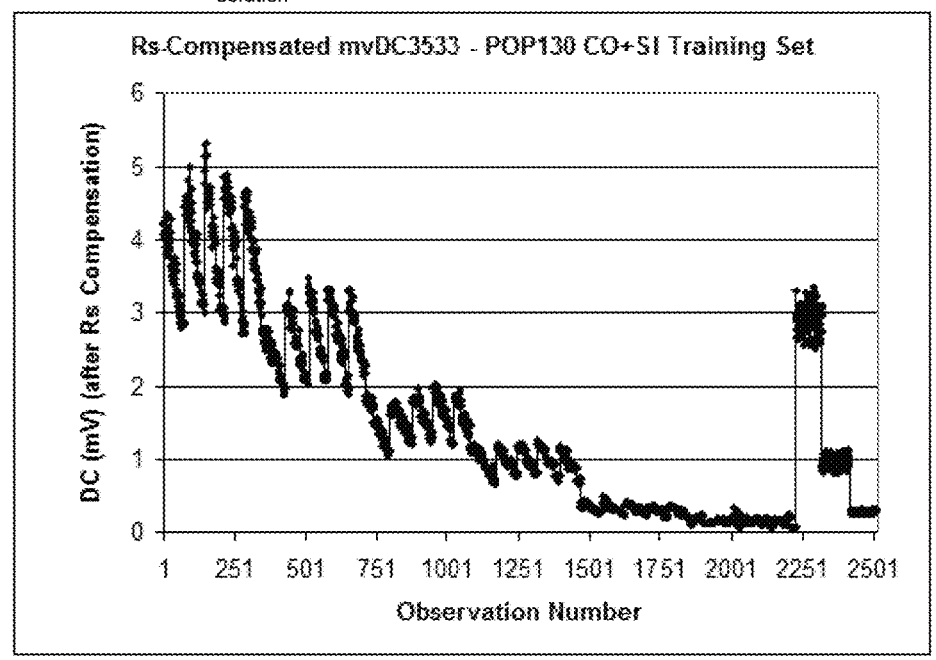

The plot of FIG. 6D shows no trending of the new admittance values at any of the four measured frequencies. The plot of FIG. 6E shows a direct relationship to temperature and also shows that the precision of the new admittance value, by frequency, is greatly improved. Also, the new admittance values for the salt-containing samples are more similar to other surrounding samples.

To evaluate the effect of $R_{solution}$ scaling of DC measurement data, the dataset was sorted in order of decreasing glucose level, then by decreasing Hct level, and then by decreasing temperature. The plot of FIG. 6C shows a single measured DC current value (from the last pulse in the applied potential sequence) plotted for each sample in the sorted data set. The last three levels in the plot correspond to the spiked plasma samples with different salt concentrations.

From the sorted plot of DC current for the glycolized venous blood samples, it is possible to detect the six (6) glucose levels and five (5) Hct levels present in the data. Within each glucose level, notice that the highest (first) Hct level contains lower DC current values, and the lowest (last) Hct level contains higher DC values. In contrast, the effect of $R_{solution}$-scaling/compensation of the DC current values can be readily seen in the plot of FIG. 6F. In particular, the Hct levels ("spikes") within each glucose level have magnitudes that are much more similar across all Hct levels.

Example 2

The Factor Scaling Method

Figure 7:
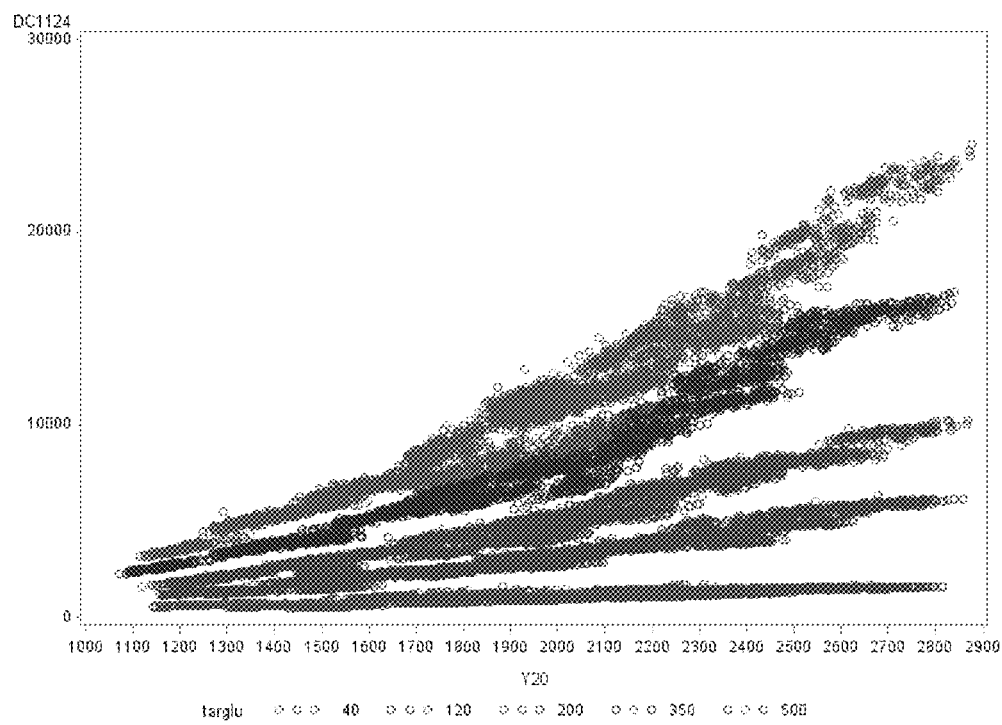
FIG. 7 is a graph showing the relationship between a DC current measurement (DC1124) and an admittance ($Y_{20}$).

A second exemplary scaling method is based upon a direct scaling of DC current measurements using the admittance at 20 kHz. FIG. 7 shows a relationship between a given DC current value and the measured admittance at 20 kHz ($Y_{20}$). As described above, the measured $Y_{20}$ is dependent upon both Hct level and temperature. Due to the impact of Hct and temperature, a given DC magnitude can correspond to more than one glucose level. The second exemplary scaling method therefore is based upon computing a new angle, $\theta$, formed between a selected DC current value and the corresponding $Y_{20}$ for the same sample. The value of $\theta$ is calculated according to the following equation:

$$\theta = \arctan(DC/Y20).$$

Figure 8:
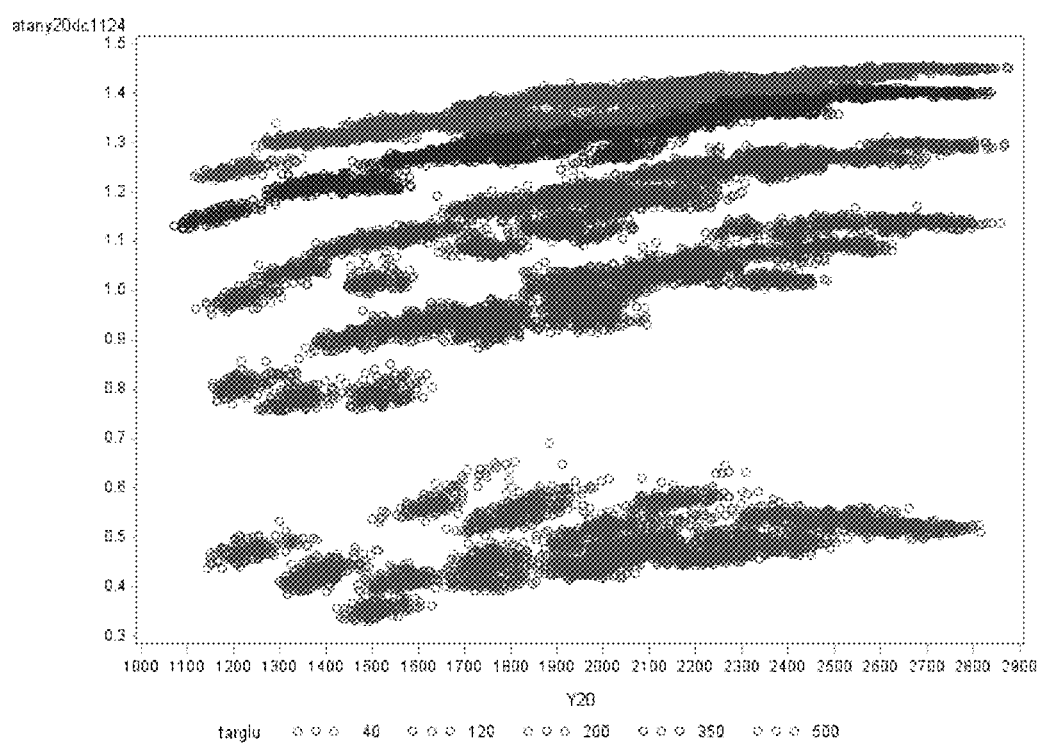
FIG. 8 is a graph showing the relationship between a phase angle ($\theta$) and an admittance ($Y_{20}$).

The second exemplary scaling method produces a situation in which $\theta$ is "orthogonal" to the $Y_{20}$, as seen in FIG. 8, thereby seeking to minimize the impacts of Hct and temperature in the new variable. This impact is minimized because the surface generated by $\theta$, $Y_{20}$, and glucose level is smoother in FIG. 7 than in FIG. 8.

Example 3

The "Power" Scaling Method

A third scaling method is based upon the scaling of a DC current value by a $Y_{20}$ raised to an optimized power, where the power term ranges typically from 0 to 10. This scaling method can be performed in accordance with the following equation:

$$\text{scaled DC} = DC/Y_{20}^{optimized\ power}.$$

The rationale behind this approach is that both DC and $Y_{20}$ are dependent on Hct and temperature, while only DC is dependent on glucose concentration in the test sample. By scaling DC current with $Y_{20}$, adjusted with certain power, Hct- and temperature-dependence can thus be removed from DC while glucose dependence is still preserved.

Figure 9:
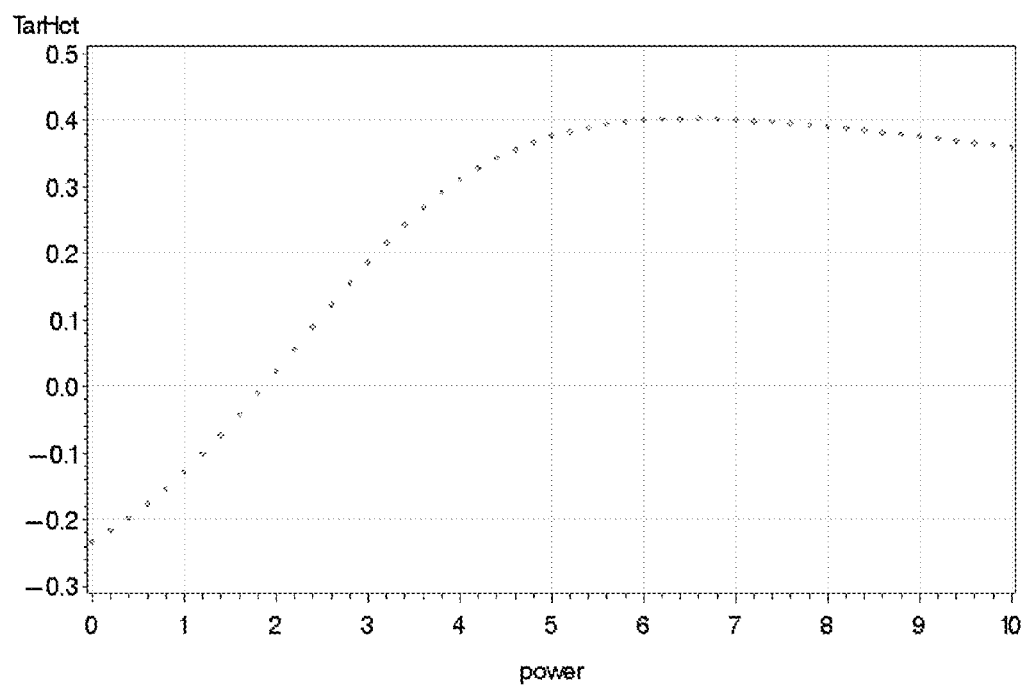
FIG. 9 is a graph showing a Pearson correlation between scaled DC and a power term.
Figure 10:
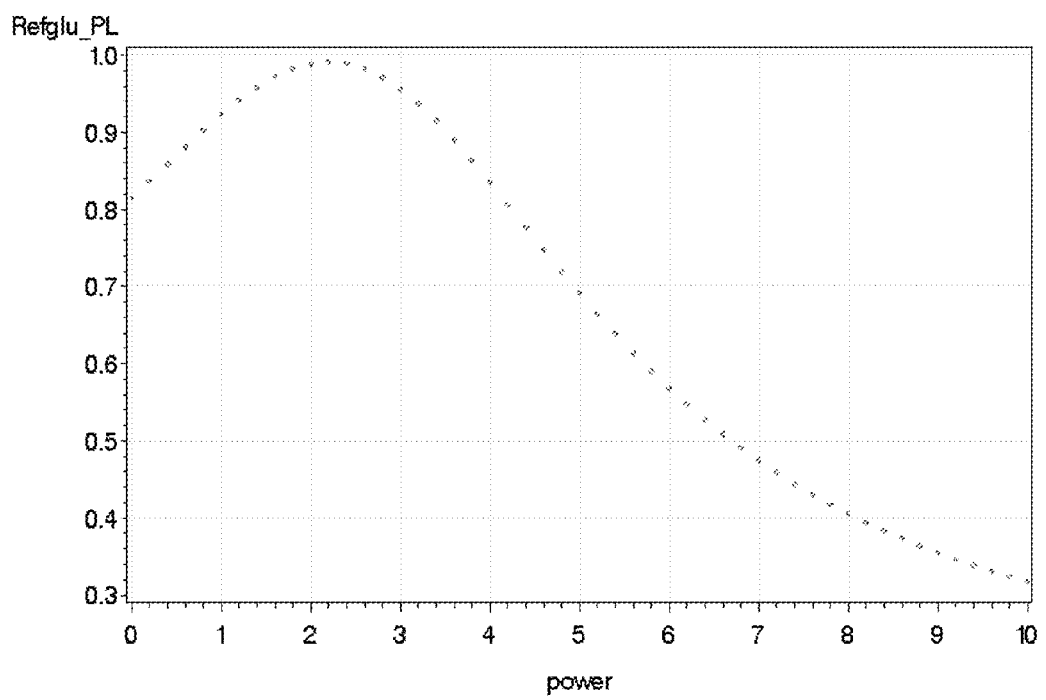
FIG. 10 is a graph showing a Pearson correlation between scaled DC and a power term.

The power term is optimized through Pearson correlation score as shown in FIGS. 9-10. The power has been iterated between 0 and 10. DC3533 (the DC current measured at 3.533 seconds after sample sufficiency) was used in demonstrating this method. At each chosen power, a Pearson correlation was calculated between the scaled DC current and one of the three variables of interest—Hct (shown at Tarhct), temperature (shown as Condition_T) and glucose concentration (shown as refglu_PL). For example, it can be observed when power approaches 2, the Pearson correlation score between scaled DC current and Tarhct is near zero.

Example 4

The $R_{conductor}$ Scaling Method

A fourth scaling method is based upon measuring at least two loop resistances of a biosensor electrode system and then normalizing each of the loop resistances to correct and/or compensate electrode conductivity variations including conductive layer thickness variations. The rationale behind this approach is that loop resistances can, and will vary, and that non-uniform variations can affect an analyte concentration.

Referring once again to FIG. 2, the electrode system can include any number of different electrodes, including test meter contact pads and electrically conductive trace portions, which thereby form resistance loops. For example, one illustrated electrically conductive pathway can include a working electrode 121, working electrode contact pads 123a and 123b and conductive trace portions 125a and 125b that extend between and electrically couple working electrode 121 and working electrode contact pads 123a and 123b. Another electrically conductive pathway includes a counter electrode 120 (illustrated as comprising dual prongs), counter electrode contact pads 124a and 124b, and conductive trace portions 126a and 126b that extend between and electrically couple counter electrode 120 and counter electrode contact pads 124a and 124b.

Figure 11:
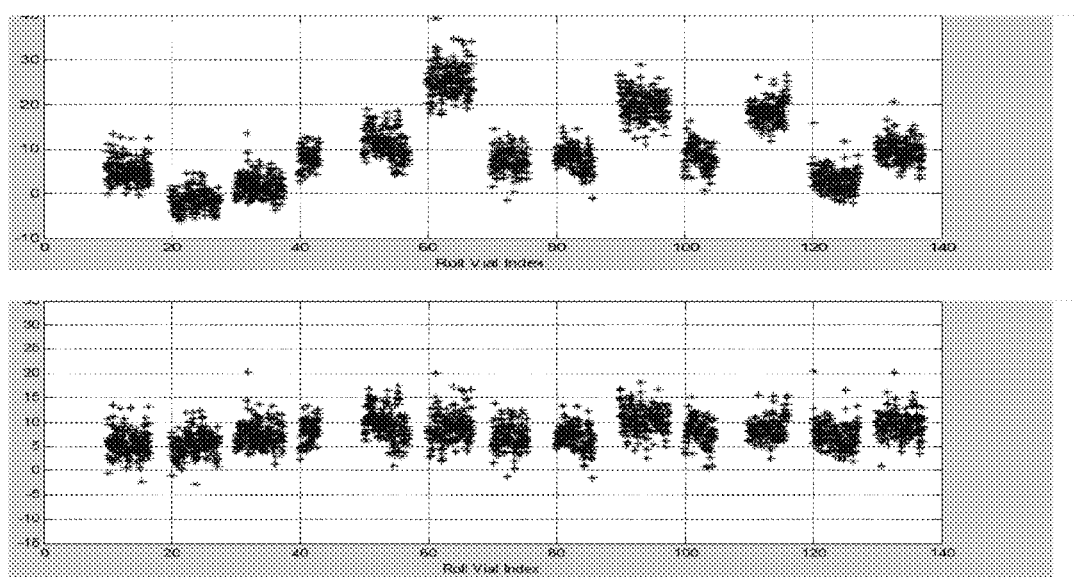
FIG. 11 is two graphs showing benefits of $R_{conductor}$ scaling for variations in electrode conductivities.

FIG. 11 shows the difference of the performance with and without $R_{conductor}$ scaling for DC block measurements obtained from a sample having a glucose concentration of about 120 mg/dL. The upper panel shows the results from thirteen (13) different lots of materials with different conductivities, where calculated analyte concentrations vary significantly. In the bottom panel, $R_{conductor}$ was applied, and the variations were significantly reduced. In FIG. 11, the y-axis is bias to the reference glucose concentration, and the x-axis is the individual lot of biosensors.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

The invention claimed is:

1. A method of scaling amperometric data obtained during an electrochemical analysis of an analyte of interest to compensate for variations in electrode conductivity, the method comprising the steps of:
    applying an electrical test sequence to a body fluid sample in an electrochemical biosensor, the biosensor comprising:
        an electrode system,
        a reagent in electrical communication with the electrode system, and
        a receptacle configured to contact the fluid sample provided to the biosensor,
    wherein the test sequence comprises at least one AC block of low-amplitude signals and at least one DC block, and wherein the body fluid sample comprises the analyte of interest;
    measuring AC and DC current responses to an electroactive species indicative of the analyte of interest;
    measuring at least two loop resistances of the electrode system of the biosensor, wherein a first loop resistance is measured between two contact pads associated with a trace of a working electrode, and wherein a second loop resistance is measured between two contact pads associated with a trace of a counter electrode;
    normalizing the at least two loop resistances ($R_{conductor}$) by dividing a first loop resistance by a first constant and by dividing a second loop resistance by a second constant to obtain normalized loop resistances;
    scaling the amperometric data by incorporating the lowest normalized loop resistance into an algorithm for determining an analyte concentration or a failsafe calculation.

2. The method of claim 1, wherein the AC block comprises a multi-frequency excitation waveform of at least two different frequencies.

3. The method of claim 2, wherein the frequencies are about 10 kHz, about 20 kHz, about 10 kHz, about 2 kHz and about 1 kHz, and wherein each is applied for about 0.5 sec to about 1.5 sec.

4. The method of any of claim 1, wherein the at least one DC block includes at least one pulse to about ten pulses at a potential that alternates between about 0 mV to about +450 mV, and wherein each pulse is applied for about 50 msec to about 500 msec.

5. The method of claim 4, wherein each DC pulse at about +450 mV is applied for about 250 msec, and each DC pulse at about 0 mV is applied for about 500 msec.

6. The method of claim 1, wherein the first constant and the second constant are a pre-determined median resistance value.

7. The method of claim 1 further comprising the step of estimating the analyte concentration based upon scaled amperometric data.

8. The method of claim 1 further comprising the step of providing a failsafe that incorporates $R_{conductor}$ as a parameter into a failsafe algorithm, wherein the failsafe prevents reporting or displaying of the analyte concentration if the variations in electrode conductivity are above a predetermined threshold.

9. The method of claim 1, wherein the analyte concentration is a glucose concentration.

10. The method of claim 1, wherein the variations in electrode conductivity are selected from the group consisting of variations in conductive layer thickness within the electrode system, scratches within the electrode system, defects within the electrode system, and contact resistance variations between biosensor contact pads and a meter contact.

* * * * *